(12) United States Patent
Selby et al.

(10) Patent No.: US 8,052,986 B1
(45) Date of Patent: *Nov. 8, 2011

(54) SYSTEM CONTROLLING SOLUBLE PHOSPHORUS

(75) Inventors: E. Field Selby, Conway, AR (US); John R. Hardee, Arkadelphia, AR (US); Joe D. Henry, Little Rock, AR (US)

(73) Assignee: EnviroVest LLC

( * ) Notice: Subject to any disclaimer, the term of this patent is extended or adjusted under 35 U.S.C. 154(b) by 740 days.

This patent is subject to a terminal disclaimer.

(21) Appl. No.: 11/972,272

(22) Filed: Jan. 10, 2008

Related U.S. Application Data (63) Continuation-in-part of application No. 11/182,275, filed on Jul. 15, 2005, now Pat. No. 7,537,789.

(51) Int. Cl.
*A01N 25/32* (2006.01)

(52) U.S. Cl. .......... 424/406; 71/13; 71/61; 71/62; 71/63; 71/64.08; 424/709; 588/221

(58) Field of Classification Search .......... 424/709
See application file for complete search history.

(56) References Cited

FOREIGN PATENT DOCUMENTS
EP 787540 * 8/1997
* cited by examiner

*Primary Examiner* — Neil Levy
(74) *Attorney, Agent, or Firm* — Joe D. Calhoun; Rashauna A. Norment (57) ABSTRACT

An aqueous alkali earth metal salt solution useful as an activator for mixing thoroughly with chicken litter or similar animal waste containing excessive amounts of soluble phosphorus and nitrates. When used as a prelude to treatment with an alkali metal silicate based solution, the aqueous alkali earth metal salt solution greatly increases the chemical binding of the soluble phosphorus and/or nitrates present in the animal waste or nearby environment such as soil or water.

10 Claims, 4 Drawing Sheets

$\sigma$-P Removal From Littler Treatment

| Treatment Mixture | P concentration (ppm) | % P removal |
|---|---|---|
| Chicken Litter only (Control) | 8,990 | 0.0 |
| 17% SB & 5% "Activator" | 2,230 | 75.2 |
| 17% SB"RF" & 5% "Activator" | 2,440 | 72.9 |
| Mean (x) % Removal | | 74.1 |
| S. D. | | +/- 1.626 |

Reference: Vanadomolybdophosphoric Acid Method

Fig. 1 – Percentage σ-P Removal From Aqueous Solution

| Weight of SB Activator | Volume | σ-P Concentration ppm | %P Reduction |
|---|---|---|---|
| 2.5g | 5 ml SB "RF" | 1,750 | 30 |
| 2.5g | 10 ml SB "RF" | 975 | 61 |
| 2.5g | 5 ml SB | 1,700 | 32 |
| 2.5g | 10 ml SB | 225 | 91 |
| 4.9g | 5 ml SB "RF" | 1,375 | 44 |
| 4.9g | 10 ml SB "RF" | 325 | 87 |
| 4.9g | 20 ml SB "RF" | 75 | 97 |
| 4.9g | 5 ml SB | 575 | 77 |
| 4.9g | 10ml SB | 1,800 | 28 |

Fig. 2 – σ-P Removal from Litter Treatment

| Treatment Mixture | P concentration (ppm) | % P removal |
|---|---|---|
| Chicken Litter only | 230 | |
| 10% SB™ & 5% "Activator" | 80 | 65 |
| 17% SB™ & 5% "Activator" | 120 | 48 |
| 10% SB"RF" & 5% "Activator" | 160 | 30 |
| 17% SB"RF" & 5% "Activator" | 70 | 70 |

Reference: Vanadomolybdophosphoric Acid Method

Fig. 3 – σ-P Removal from Litter Treatment

| Treatment Mixture | P concentration (ppm) | % P removal |
|---|---|---|
| Chicken Litter only | 540/550 | |
| 10% SB"RF" & 5% "Activator" | 120 | 78 |
| 17% SB"RF" & 5% "Activator" | 130 | 76 |
| Mean (x) % Removal | | 74.67 |
| S.D. | | +/- 4.16 |

Reference: Vanadomolybdophosphoric Acid Method

Fig. 4 – σ-P Removal From Littler Treatment

| Treatment Mixture | P concentration (ppm) | % P removal |
|---|---|---|
| Chicken Litter only (Control) | 8,990 | 0.0 |
| 17% SB & 5% "Activator" | 2,230 | 75.2 |
| 17% SB"RF" & 5% "Activator" | 2,440 | 72.9 |
| Mean (x) % Removal | | 74.1 |
| S. D. | | +/- 1.626 |

Reference: Vanadomolybdophosphoric Acid Method

Fig. 5 - Comparison of 10% Activator and SB for Binding Phosphorus and Nitrate

| Analysis | Control (ppm) | Treated Litter (ppm) | Reduction |
|---|---|---|---|
| SPLP Nitrate | 4.42 ± 0.24 | 4.03 ± 0.26 | 9% |
| SPLP Soluble Phosphorus | 195 ± 9 | 63 ± 10 | 68% |
| SPLP Total Phosphorus | 281 ± 6 | 114 ± 10 | 59% |

SPLP - EPA 1312 Extraction Method

Fig. 6 - Comparison of 5% Activator and SB for Binding Phosphorus and Nitrate

| Analysis | Control (ppm) | Treated Litter (ppm) | Reduction |
|---|---|---|---|
| SPLP Nitrate | 4.42 ± 0.24 | 4.42 | 0% |
| SPLP Soluble Phosphorus | 195 ± 9 | 28 | 86% |

SPLP - EPA 1312 Extraction Method

Fig. 7

Effect on SPLP Nitrate Reduction of Varying Volumes of ProAgri
(100 mL of 5% Activator per 100 g. Chicken Litter)

Volume ProAgri / mL per 100 g Chicken Litter

Fig. 8

Effect of Varying Volumes of ProAgri on SPLP Soluble Phosphorus Reduction
(100 m/L 5% Activator per 100 g. Chicken Litter Volume ProAgri / mL per 100 g of Chicken Litter

SYSTEM CONTROLLING SOLUBLE PHOSPHORUS

CROSS REFERENCE TO RELATED APPLICATIONS

This is a continuation-in-part application of co-pending U.S. utility patent application Ser. No. 11/182,275 filed 15 Jul. 2005 and subject to special examination pursuant to the Order granting the Petition to Make Special, the benefit of which is claimed to the extent possible.

FEDERALLY SPONSORED RESEARCH AND DEVELOPMENT

Not applicable.

MICROFICHE APPENDIX

Not applicable.

BACKGROUND OF THE INVENTION (1) Field of the Invention

The present invention generally relates to systems of chemicals and solutions for controlling substances that are nutrients for plants and microorganisms when available in optimal amounts, but which are considered contaminants when available in overabundance. Such control may optimize the use of abundant animal waste as fertilizers, without adversely affecting surface water. The invention described and claimed herein essentially binds soluble phosphorus and nitrates commonly found in animal waste and fertilizers (and the soil upon which those are spread), rendering them unavailable for contaminating adjacent soil and water. More preferably, the present invention involves solutions that bind soluble phosphorus and nitrates commonly found in animal waste and fertilizers (and the soil upon which those are spread), rendering them unavailable for leaching into adjacent soil or water. These compositions bind soluble phosphorus (pre-existing in chicken litter) into inert matrices, essentially or practically permanently, thereby functionally removing soluble phosphorus from the chicken litter. Moreover, the present invention relates to treatments for soil including chicken litter or other animal waste. The present invention also includes methods of using said solutions, and methods of using the combination of said solution(s) and animal waste treated therewith to provide a fertilizer or soil addendum.

This invention relates to a system for controlling the availability of plant nutrients and perhaps other growth factors, together with the method of using the contaminant remedial composition. Contamination of soil and water, by pollutants or even by an overabundance of otherwise neutral or beneficial substances, are serious environmental concerns at this time. Great concern has been expressed for decades over the accumulation and disposal of wastes, especially those accumulating during the mass-production of poultry, cattle, swine and other animals. Substances commonly found or accumulating in soil and water include soluble phosphorus, nitrates, arsenic and selenium. Moreover, although most of those substances are considered to be beneficial plant nutrients (or growth factors for microorganisms) when present in optimal quantities, overabundance may result in over-growth of plants and microorganisms that can themselves harm soil (or nearby surface water).

In one typical scenario, chicken litter in poultry houses accumulates with an overabundance of moisture, ammonia, dust and microbes, adversely affecting animal health. That chicken litter often is removed and used as fertilizer, because of its high content of plant nutrients. Constituents such as soluble phosphorus and nitrates often leach into surface waters and spawn aquatic overgrowth, causing environmental problems such as eutrophication of water sources. The present invention both optimizes the availability of plant nutrients for crop growth and reduces (or prevents) the growth of algae and other plants associated with eutrophication.

(2) Description of Related Art Including Information Disclosed 37 CFR 1.97 and 1.98

Known in the art are various pollution remedial compositions. For example, the following patents and unpatented products are arguably related to the patentability of the subject invention:

U.S. Pat. No. 5,478,389 issued to Loomis discloses a pollution remedial composition comprising a soluble silicate (preferably sodium silicate), a surfactant, a polyol and water. The Loomis composition may also include sodium chloride and citric acid, and possibly glycerine. Loomis does not disclose the application of any such composition to animal waste or any other substance or substratum containing an overabundance of phosphorus, nitrates, moisture, ammonia, arsenic, selenium, dust particles or microbes, nor is any such application inherent in Loomis.

Some known products such as Alum and AlClear are known to use aluminum sulfate to reduce ammonia and/or soluble phosphorus in chicken litter. However, an excessive level of aluminum sulfate is harmful to soil and animal health. Another such product, PLT, reduces ammonia in chicken litter, but has been shown to be corrosive to metals.

BRIEF SUMMARY OF THE INVENTION

One general version of the present invention comprises (includes) a solution for spraying on substrate contaminated with soluble phosphorus and/or nitrates (such as chicken litter), to bind such ortho-phosphate and prevent it from later becoming re-dissolved. Although the invention has several embodiments, one basic embodiment also includes an activator for applying to the contaminated substrate, then spraying an aqueous solution of alkali metal silicate for immobilizing the migration of soluble phosphorus.

In a more detailed version of the invention, before being applied to the phosphorus-contaminated substrate, an aqueous solution of the following is prepared: an alkali metal silicate; an anionic surfactant such as an ester of organo-phosphoric acid; and a polyol such as polypropylene glycol. An alkaline earth metal salt based activator may be applied to the substrate before application of that aqueous solution. Such compounds include calcium acetate, magnesium nitrates or barium chloride.

It is believed that the process involves conversion of soluble phosphorus, resulting in the chelating of phosphorus for the formation of an inert dehydrated phospho-silicate apatite. The silicate is believed to be a binding agent, for binding metal cations in a stable complex. When metal cations such as alkaline earth cations exchange with alkali metal cations, a charge imbalance is created in the silicate complex with the result that phosphorus is incorporated in the complex and rendered unavailable for further reaction with other reagents.

One primary object of the present invention is to provide a new and effective composition for controlling the availability of plant nutrients in soil, together with a method of using the composition.

Another primary object of the present invention is to provide a composition for adding growth factors to soil, such as a fertilizer or soil amendment, together with a method of using same.

It is another object of the present invention to provide a composition that can effectively reduce the soluble phosphorus content of chicken litter and other animal waste, or the soil upon which such waste is situated.

It is another object of the present invention to provide a composition that can effectively reduce the soluble nitrate content of chicken litter and other animal waste, or the soil upon which such waste is situated.

It is yet another object of the present invention to provide a composition that can effectively reduce the arsenic content of chicken litter and other animal waste, or the soil upon which such waste is situated.

It is also an object of the present invention to provide a composition that can effectively reduce the selenium content of chicken litter and other animal waste, or the soil upon which such waste is situated.

It is another object of the present invention to provide a composition that can effectively reduce the amount or concentration of moisture, airborne dust and microbes in animal confines such as poultry houses, feed lots and other areas of animal concentration.

It is still another object of the present invention to provide a composition that can effectively reduce the ammonia concentrations in animal confines such as poultry houses, feed lots and other areas of animal concentration.

Other objects will be apparent from a reading of the written description disclosed herein, together with the claims.

These drawings illustrate certain details of certain embodiments. However, the invention disclosed herein is not limited to only the embodiments so illustrated. The invention disclosed herein may have equally effective or legally equivalent embodiments.

DETAILED DESCRIPTION OF THE INVENTION

For the sake of simplicity and to give the claims of this patent application the broadest interpretation and construction possible, the following definitions will apply:

The term "plant nutrient" or derivative thereof essentially means phosphorus and nitrates in a form acceptable to plant metabolism.

The term "growth factor" or derivative thereof essentially means the plant nutrients (soluble phosphorus and nitrates), arsenic and/or selenium.

Also for the sake of simplicity, the conjunctive "and" may also be taken to include the disjunctive "or," and vice versa, whenever necessary to give the claims herein the broadest interpretation and construction possible. Likewise, when the plural form is used, it may be taken to include the singular form, and vice versa.

The invention disclosed herein is not limited by ingredients to the extent that such materials satisfy the structural and/or functional requirements of any claim.

Although the invention has a number of features and variations, its most general form includes (comprises) a composition for controlling the availability of plant nutrients in soil, comprising an aqueous alkali metal silicate. Said plant nutrients may be selected from the group consisting of soluble phosphorus and nitrates, and combinations and mixtures thereof. Each of said substances has a common characteristic justifying its inclusion in this group, namely, these otherwise beneficial substances may be present in such high concentrations as to present environmental concerns. One main version of the invention affects the plant nutrient soluble phosphorus.

One general version of the invention is a composition wherein said aqueous alkali metal silicate is selected from the group consisting of sodium silicate and potassium silicate, and combinations and mixtures thereof. Each of said substances has a common characteristic justifying its inclusion is this group, namely, acting as a binding agent for binding metal cations in a stable complex. Said aqueous alkali metal silicate may include aqueous sodium silicate at a concentration in the range of between about 1% and 42% by weight of the composition (solution). Alternately, said aqueous alkali metal silicate may be aqueous potassium silicate at a concentration in the range of between about 1% and 42% by weight. One preferred embodiment may include aqueous alkali metal silicate in a concentration in the range of between about 19% and 23% by weight, preferably about 20.8% by weight.

One preferred method involves a 20.8% solution of silicate blend (such as sodium silicate), applied in the ratio of about 0.2 liter of silicate blend solution to about 1 kilogram of litter to be treated, with mixing.

Said soluble phosphorus may include (comprise) solid animal waste and, if so, said availability of plant nutrients may be reduced by up to 50%.

Another version of the invention further includes an activator, greatly enhancing the effectiveness, resulting from unexpected synergies attributable to the presence of said activator. Said plant nutrients may be selected from the group consisting of phosphorus and nitrates, and combinations and mixtures thereof. Said plant nutrient may include soluble phosphorus, and said activator may include an aqueous alkaline earth metal salt. More particularly, said aqueous alkaline earth metal salt may be selected from the group consisting of water soluble alkaline earth metal salts, such as (for example) sulfates, nitrates, chlorides and acetates, and combinations and mixtures thereof. Said soluble alkaline earth metal salt may be magnesium sulfate at a concentration of between about 1% and 20% by weight of the activator (solution). Alternatively, said soluble alkaline earth metal salt may be calcium nitrates at a concentration of between about 1% and 20% by weight.

In the event the treatment context permits an activator to be applied to the chicken litter as a prelude to applying the silicate blend, one preferred method involves a 5% solution of magnesium sulfate (by weight of activator solution), applied in the ratio of about 1 liter of activator to about 1 kilogram of litter to be treated, with mixing. Another preferred method involves a 10% solution of magnesium sulfate applied in the ratio of about 0.5 liter of activator to about 1 kilogram of litter, with mixing.

When using one of the above described compositions, and said soluble phosphorus includes solid animal waste, said availability of plant nutrients may be reduced by up to 86%.

Another version of the invention includes a composition described above wherein said plant nutrient is nitrate. When using one of the above described compositions, and said soluble phosphorus and nitrates includes solid animal waste, said availability may be reduced considerably; said soluble phosphorus may be reduced by up to 86%, and said nitrates may be reduced by up to 99%.

Another version of the invention further includes a surfactant and/or a polyol. More particularly, said surfactant may include an anionic surfactant, preferably selected from the group consisting of phosphate esters, and combinations and mixtures thereof. Each of said substances has a common characteristic justifying its inclusion is this group, namely, lowering the surface tension of the aqueous alkali metal silicate solution. Even more particularly, said surfactant may be ester of organo-phosphoric acid, preferably in a concentration range of between about 1% and 5% by weight of the aqueous alkali metal silicate composition. Even more particularly, said ester of organo-phosphoric acid may be in a concentration range of about 1% by weight.

Said polyol may be propylene glycol, preferably in a concentration range of about 1% by weight of the aqueous alkali metal silicate composition.

Another version of the invention includes a composition for adding growth factors to soil. Besides the aforementioned plant nutrients (phosphorus and nitrates), said growth factors may be selected from the group also consisting of moisture, ammonia, arsenic, selenium, dust particles and microbes, and mixtures and combinations thereof. Each of said substances has a common characteristic justifying its inclusion is this group, namely, substances present in poultry litter or animal waste that, when accumulated or aggregated, is harmful to the environment. This version of the invention essentially manifests additional utility through an independent, secondary use of the above described treatment compositions, as a soil amendment or fertilizer. The present invention is capable of preserving (in the animal waste) enough of the nutrients necessary for plant growth, but reducing concentrations that may produce negative environmental impact. One such version includes a combination of animal waste treated with one of the above described treatment compositions for controlling the availability of said growth factors in said animal waste. More particularly, said treatment composition may include an aqueous alkali metal silicate. Said aqueous alkali metal silicate may be aqueous sodium silicate at a concentration in the range of between about 1% and 42% by weight. Alternatively, said aqueous alkali metal silicate may be aqueous potassium silicate at a concentration in the range of between about 1% and 42% by weight.

Said growth factor may be soluble phosphorus and, if said soluble phosphorus is included in solid animal waste (such as chicken litter, for example), said availability may be reduced by up to 50%.

Another version of this soil addendum version may further include an activator, especially including an aqueous alkaline earth metal salt. Said aqueous alkaline earth metal salt may be selected from the group consisting of water soluble alkaline metal salts such as (for example) sulfates, nitrates, chlorides and acetates, and combinations and mixtures thereof. More particularly, said soluble alkaline earth metal salt may include magnesium sulfate at a concentration of between about 1% and 20% by weight. Alternatively, said soluble alkaline earth metal salt is calcium nitrates at a concentration of between about 1% and 20% by weight. When said soluble phosphorus is included in solid animal waste, said availability is reduced by up to 86%.

Said growth factor may include nitrate. When said soluble phosphorus and nitrates are included in solid animal waste, and said availability may be reduced considerably; said soluble phosphorus may be reduced by up to 86%, and said nitrates may be reduced by up to 99%.

In one particular version of a soil amendment version of the invention, said animal waste comprises chicken litter, said soluble alkaline earth metal salt comprises magnesium sulfate at a concentration of between about 1% and 20% by weight, and said growth factor comprises arsenic. In another particular version of a soil amendment version of the invention, said animal waste comprises turkey litter, said soluble alkaline metal salt comprises calcium acetate at a concentration of between about 1% and 20% by weight, and said growth factor comprises selenium. In yet another particular version of a soil amendment version of the invention, said animal waste comprises hog manure, said soluble alkaline metal salt comprises barium chloride at a concentration of between about 1% and 20% by weight, and said growth factor comprises nitrates.

As with the plant nutrient controlling version of the invention, the soil amendment version may also include a surfactant and/or a polyol; said surfactant may include an anionic surfactant, especially selected from the group consisting of phosphate esters, and combinations and mixtures thereof. Said surfactant may be an ester of organo-phosphoric acid, especially in a concentration range of between about 1% and 5% by weight. More particularly, said ester of organo-phosphoric acid may be in a concentration range of about 1% by weight. Similarly, said polyol may be propylene glycol, especially in a concentration range of about 1% by weight.

Besides the aforementioned compositions, the invention described herein also includes a method of using a composition for controlling the availability of plant nutrients (described above), comprising the steps of applying said composition to a substrate susceptible to exposure to unwanted levels of plant nutrients or growth factors. Alternatively, said method may further include the step of mixing the substratum to optimize uniform contact with the substratum. More particularly, said method may include the initial step of applying an activator to a substrate susceptible to exposure to unwanted levels of plant nutrients or growth factors. Even more particularly, said method may further include the step of allowing the mixed substrate to dry. The chemical reaction typically producing the best results requires a two-step process; mixing an aqueous activator into the substrate as best as possible (or practical), then mixing an aqueous sodium silicate treatment composition as best as possible (or practical).

The invention disclosed herein may also include a method of using a composition for adding growth factors to soil, comprising the step of adding to soil a combination of animal waste and a treatment composition for controlling the availability of said growth factors in said animal waste, described above.

EXAMPLE 1

It has been shown that a silicate blend ("SB") binds soluble phosphorus in the presence of SB "Activator". When the treatment sequence utilizes a natural extract from rice hulls (SB "RF"), a 97% reduction in soluble phosphorus occurs from a concentration of 2500 ppm.

Previous laboratory studies have sought to determine the relative effects of the binding capacity of SB treated litter. Treatability studies have been conducted, designed and implemented with the intent to investigate whether phosphorus in chicken litter could be prevented from leaching once treatments had been performed to chelate phosphorus and thus retard its removal.

Materials and Methods

Initial bench studies were conducted to determine the binding efficiency of SB in aqueous solution. Under these experimental conditions, soluble phosphorus was prepared in concentrations of 2500 ppm and mixed with standard solutions of SB and SB "RF" and tested for soluble phosphorus using the Vanadomolybdophosphoric Acid Method of Analysis.

Evaporation to Dryness Method

The SB and SB "RF" have proven to be extremely effective in removing phosphate from aqueous solution in bench level testing. To test these solutions they were mixed with 100 mL of 2500 ppm P (obtained by the dissolution of $KH_2PO_4$) stirred for 5 minutes, and then evaporated to dryness at 50° C. to the resulting precipitate, 100 ml of deionized water were added and stirred overnight. The aqueous portion of the rehydrated precipitate was then analyzed according to the Vanadomolybdophosphoric Acid Method.

SB Activator Method

Another effective method of removing phosphorus using these two solutions involves the addition of SB "Activator" to 100 ml of 2500 ppm P followed by the addition of either "RF" or SB original formula. These solutions were stirred for 5 minutes, left overnight, centrifuged and analyzed for phosphorus.

Results and Discussion

Analysis for phosphorus using the Vanadomolybdophosphoric Acid Method showed 99% phosphorus removal using the Original Formula (SB™) and 100% removal using the rice silicate formula (SB "RF").

Figure 1:
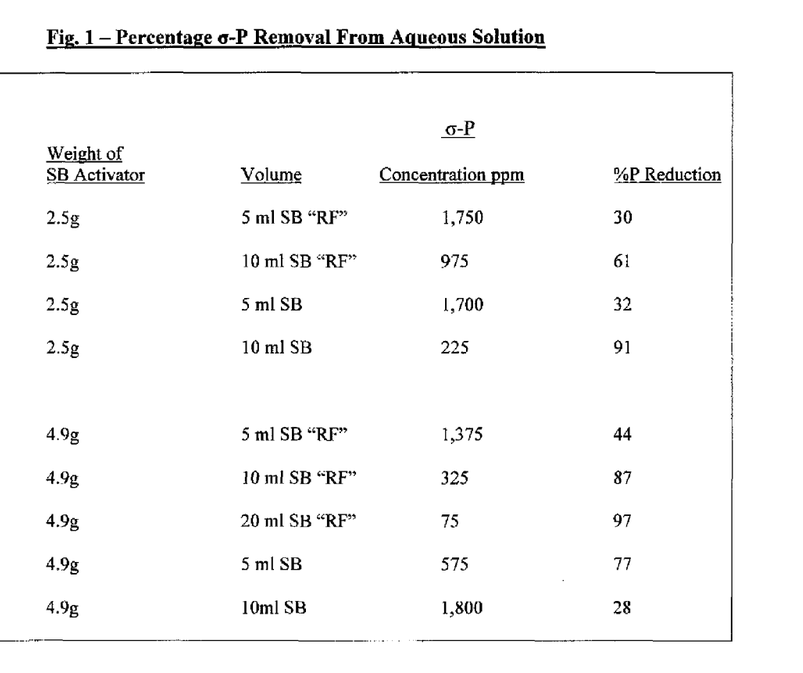
FIG. 1 is a table showing the percentage of σ-P removal from aqueous solution, in Example 1.

Results of the SB and SB "RF" in a treatment scenario using SB "Activator" were completed without drying. The table of FIG. 1 summarizes these results.

SB "Activator" alone does not reduce the phosphorus concentration. For the "RF" and the SB original formula to be effective for phosphorus removal they must be heated to dryness. In the presence of "Activator", the heating step is not necessary. A greater amount of "Activator" is needed with the "RF" than with the original formula.

Application of the preceding methodology has been adapted for the treatment of dried chicken litter at the bench level of study and testing to evaluate methods of treatment with respect to phosphorus reduction. The standard treatment protocol relies on litter obtained from a broiler house having been in use for approximately two years.

Test Procedure for Litter Treatment

Portions of the litter are retained to determine the pre-test nutrient content, that is, total P, soluble P ($\sigma$-P), and N, K, pH and dry matter:

1) Approximately 50 pounds of litter (equilibrated to room temperature and RH) were blended to a uniform mixture in a Hobart blender for 15 minutes.
2) 300 gm samples were removed from the blended sample and placed into each of 25 (9"×13") aluminum baking pans.
3) One hundred (100) gm samples (comprised of 4-25 gm sub-samples blended for three minutes) were then removed from each pan using clean plastic utensils, and placed into corresponding zip-lock bags and labeled. Four (4) sub-samples are collected for pre-test evaluation.
4) Five (5) pans were randomly treated with the following application:
    a. A stock SB "Activator" solution was prepared.
    b. 300 ml quantities of a 5% stock solution were spray applied to each of five (5) pans of litter, while hand mixing. The mixture is allowed to sit at room temperature until ready for SB application.
    a. 30 & 50 ml of undiluted SB were spray applied to the litter/"Activator" mixture, with hand mixing, until all SB has been added.
    b. 30 & 50 ml portions of an undiluted formulation using SB "RF" were spray applied to the litter/"Activator" mixture, with hand mixing, until completely blended.
5) A second set of five (5) pans were treated similarly with SB as in step 4 and a third set of five (5) pans are treated with distilled water only.
6) The samples were then placed at related temperature (~122° F./35-45% RH), uncovered to effect drying. The samples are allowed to cure* for 18-48 hours or until dry, prior to testing.
7) At the end of the drying cycle, the samples were removed in 2-100 gm* quantities and placed in plastic, zip-lock bags, labeled, and transported to the laboratory for testing.
    Eight (8) twenty-five gram samples were removed from eight different locations in the sample mixture and blended for uniformity. The samples were subdivided into 2-100 gram samples.
8) Samples were tested for total P, soluble P ($\sigma$-P), and pH. Chain-of-custody forms accompany each sample batch.

Figure 2:
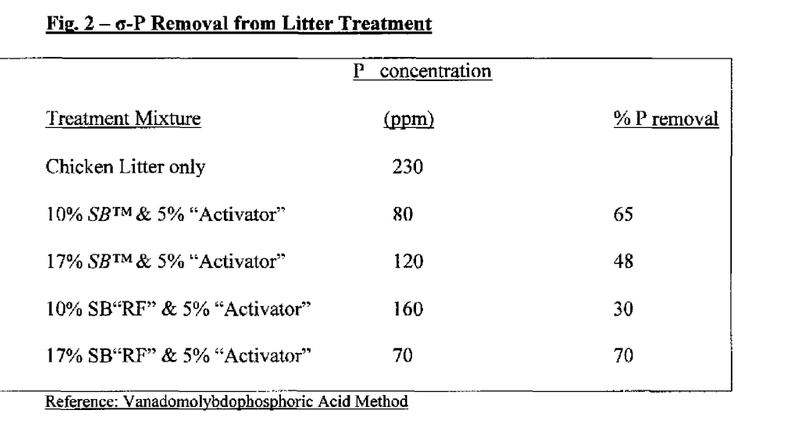
FIG. 2 is a table showing σ-P removal from litter treatment, in Example 1.
Figure 3:
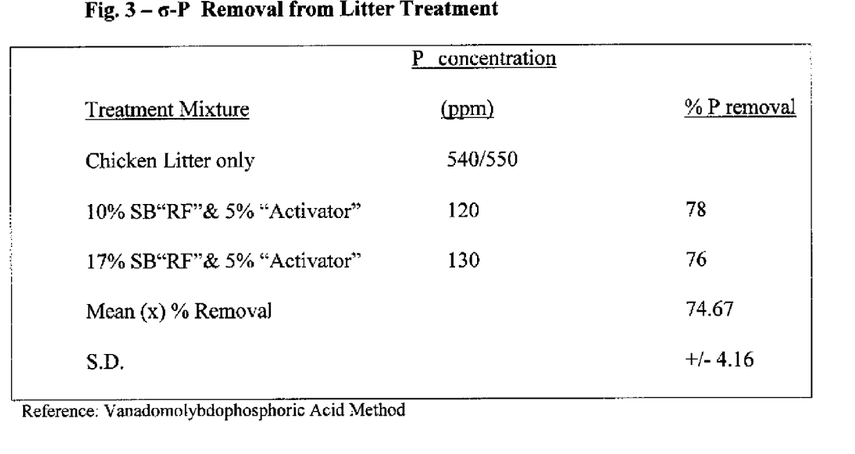
FIG. 3 is a table showing σ-P removal from a second litter treatment, in Example 1.

A second litter treatment was conducted with samples treated to replicate the treatment procedure tabulated in FIG. 2. Since the SB™ "RF" indicated a higher P removal, the treatment was conducted using "RF" and the SB™ "Activator". The results are recorded in FIG. 3.

Test Results from Mehlich III Extraction Procedure

Figure 4:
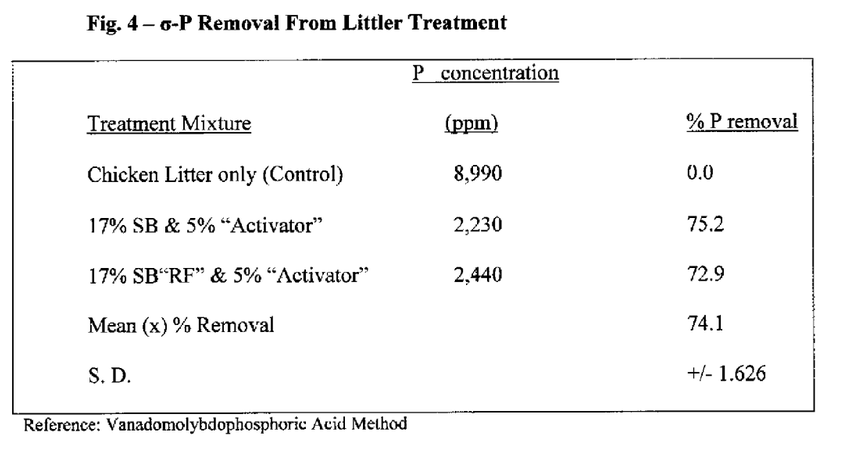
FIG. 4 is a table showing σ-P removal from a third litter treatment using the Mehlich III Extraction Procedure, in Example 1.

The Mehlich extraction procedure is an aggressive extraction procedure that measures the relative bioavailability of $\sigma$-phosphorus on acid to neutral pH soils. The test is shown to be correlated to crop response to fertilizer phosphorus. In this case, the total resident to-phosphorus loading is quantified (FIG. 4).

In the analysis, it was shown that even with this aggressive leachate procedure, 74.1% of the phosphorus remains bound and therefore not subject to runoff. If the earlier, conventional method of extraction is compared to the Mehlich II procedure, only a difference of 0.057% separates the two methods.

Conclusions

This preliminary study has been conducted under secured laboratory conditions and the results contained herein culminate bench trials designed to demonstrate the efficacy of treating soluble phosphorus solutions with environmentally non-toxic additives. The ultimate goal is to achieve total phosphorus binding in chicken litter destined for land application and thus remove the threat of leaching and runoff into surface waters.

Based on the data generated from these preliminary trials, the binding of soluble phosphorus in aqueous solution has been achieved by the use of both SB and SB "RF" formulations. The binding effects are enhanced by total evaporation to dryness at 50° C. Dryness renders silicates nearly insoluble and with their propensity for cationic exchange, reaction with other materials, such as magnesium or calcium compounds, will make the film coating completely insoluble.

The reaction has been found to be enhanced by the addition of another proprietary solution, SB "Activator". It has been found that the combination of the two products in the presence of phosphate will bind 97% of the phosphorus in aqueous solution. Similarly, preliminary bench tests to determine the effectiveness of the SB "RF" in reducing soluble phosphorus in chicken litter has produced a mean (x) 74.7% reduction using a 1:1:0.2 litter, Activator, SB mixture. The most recent test cycle (Dec. 14, 2004) establishes the tenacity of the binding process through the Mehlich III extraction procedure and confirms the repeatability and relative ease of treatment.

EXAMPLE 2

The question of whether soluble phosphorus and nitrate binding occurs during the treatment process has been addressed. A series of bench studies have been conducted to determine the binding effects of SB "Activator" formula when applied to chicken litter obtained in de-caking from brooder houses. Variables were introduced to further determine the optimal range for binding phosphorus while maintaining the nutritional demands for nitrate fertilization.

Materials and Methods

Multiple samples of chicken litter were treated initially with 5% solutions of Activator at ratios of 1:1 and 1:0.5, respectively. Added variables included the application of 10% solutions of Activator followed by the addition of SB at 20% concentration in the same treatment sequence ratio.

Figure 5:
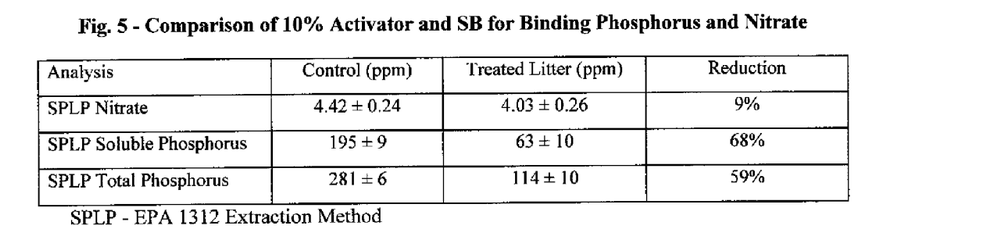
FIG. 5 is a comparison of 10% activator and SB for binding phosphorus and nitrate, in Example 2.

FIG. 5 illustrates the binding effects of SB and Activator in ratios of 0.5:0.2:1 (Activator:SB: litter) with 10% Activator solution.

Figure 6:
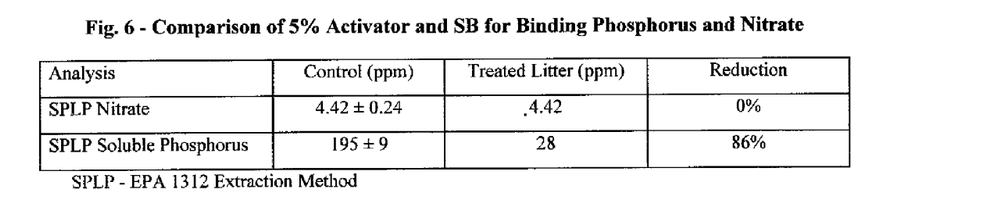
FIG. 6 is a comparison of 5% activator and SB for binding phosphorus and nitrate, in Example 2.

The data in FIG. 6 illustrates the optimal effect of phosphorus binding and ready availability of nitrate using a 5% Activator solution at a ratio of 1:0.2:1 (Activator:SB:litter).

Figure 7:
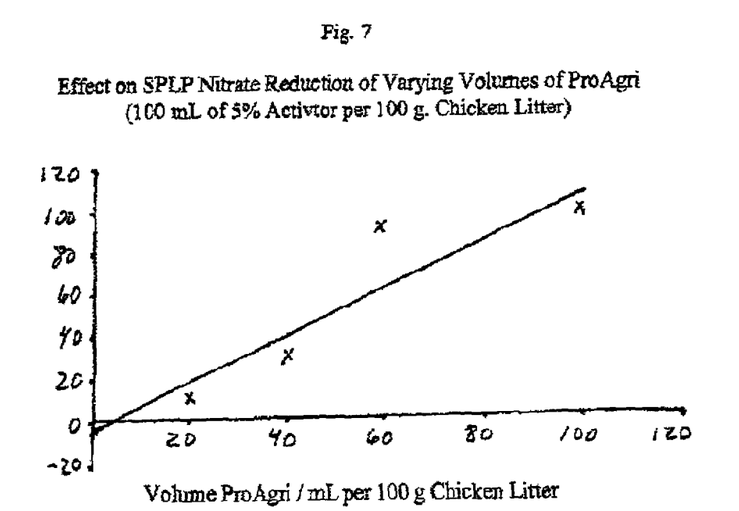
FIG. 7 is a graph depicting changes in nitrate concentration of chicken litter when treated with test solutions, in Example 2.

FIG. 7 below shows the effect on nitrate reduction of varying volumes of SB (ml of SB per 100 g of chicken litter) using a ratio of 1:1 Activator per 100 gm of chicken litter. There is an inherent flexibility using SB. Varying levels of nitrate reduction can be obtained by adjusting the volume of SB. When a 0.2:1 ratio of SB:chicken litter is used, nitrates are not significantly affected and, therefore, are still available when used as a fertilizer.

Figure 8:
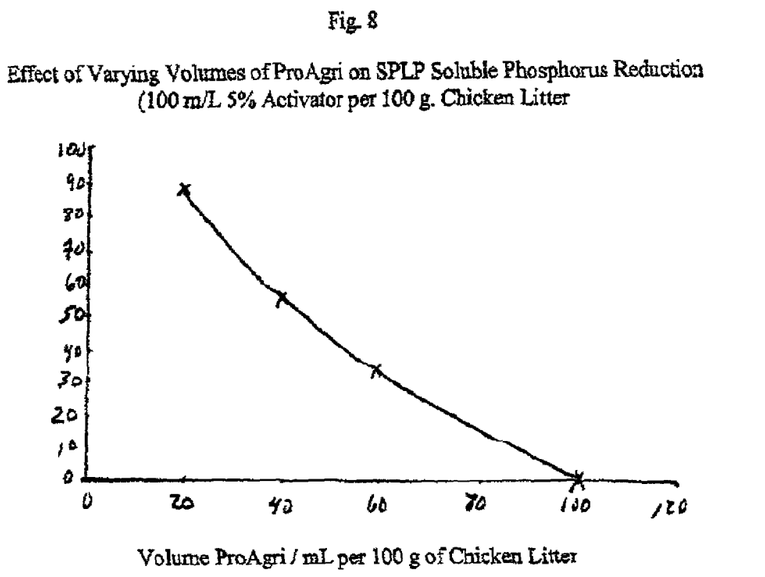
FIG. 8 is a graph depicting changes in phosphorus concentration of chicken litter when treated with test solutions, in Example 2.

The graph in FIG. 7 further illustrates that with increasing volumes of SB, nitrate reduction is proportionately increased but when compared to the effects of increased SB, the binding effects of phosphorus are diminished as shown in FIG. 8. The net effect of the appropriate application rates combine to provide excellent phosphorus reduction but allowing for no net reduction in nitrate.

The phenomenon of reduced SB gives the best results for phosphorus reduction. It is believed that larger quantities of applied SB lead to extensive polymerization that exclude phosphate rather than incorporate it into the polymer.

Conclusions

Based on the data generated from the experimental procedures for treating chicken litter using SB and Activator, it is concluded that the optimum concentration of Activator is a 5% solution applied at a ratio of 1:1. Whereas, the optimum concentration of SB is a 0.2:1 ratio SB:litter. These ratios and concentrations provide an 86% reduction in soluble phosphorus while maintaining levels of nitrate virtually intact.

The combination and use of various ratios of SB and Activator now demonstrates, at the laboratory level, the flexibility to treat chicken litter for soluble phosphorus reduction, nitrate reduction, and or both, depending on the needs of regional fertilizer applications, or the necessity to treat in favor of phosphorus reduction. This treatment capability will be to the benefit of the environment, while preserving the nutrients needed by the agricultural community, as required.

Those skilled in the art who have the benefit of this disclosure will appreciate that it may be used as the creative basis for designing devices or methods similar to those disclosed herein, or to design improvements to the invention disclosed herein; such new or improved creations should be recognized as dependant upon the invention disclosed herein, to the extent of such reliance upon this disclosure.

EXAMPLE 3

One version of the silicate blend solution is made by mixing appropriate amounts of polyol and surfactant, then mixing that solution with an appropriate amount of water. Aqueous alkali metal silicate is then added to the mixture, until the desired concentration of aqueous alkali metal silicate is obtained. One preferred concentration is a solution of between about 20% and 21% aqueous sodium silicate. For example, for making a 275 gallon batch of the silicate blend from a stock of aqueous sodium silicate containing sodium silicate solids of between about 25% and 26%, 1.9 gallons of propylene glycol are mixed with 1.9 gallons of ester of organo-phosphoric acid (such as sold under the T-Mulz brand). That 3.8 gallon mixture is then added to approximately 36 gallons of water, and mixed well. Then about 235.2 gallons of aqueous sodium silicate solution are added and mixed, to yield aqueous sodium silicate solution having a final concentration of between about 20% or 21% (typically about 20.8%). Such silicate blend may then be sprayed on chicken litter, and mixed therein as best as practicable. Typically the amount of silicate blend applied will treat a volume of chicken litter approximately one-half inch deep.

EXAMPLE 4

Two poultry houses (Test House 1 and Control House 2), each having floor dimensions of 40 feet by 500 feet already covered by a bedding consisting of an existing combination of rice hulls and pine shavings. Each house had previously hosted a separate flock of the same number of broiler chickens, for a 63-day grow-out cycle; prior to treatment, the resulting mixture of chicken litter and bedding was then "caked out" in according with standard industry practices. One application of silicate blend was performed on the litter in Test House 1 prior to placement of the test flock in the house. Samples of litter were collected:

(A) 5 days prior to placement of the test flock in the house; then (B) at day 44 of the grow-out period; and finally (C) 2 days after the end of the grow-out period (after removal of the test flock, and before de-caking). All samples were analyzed for content of soluble phosphorus, according to the EPA SW846—Method 1312 (Synthetic Precipitation Leaching Procedure, "SPLP") by a commercial laboratory. The SPLP method of extraction is an EPA 1312 procedure used to determine leachate metals in soil during rainfall events and runoff. The procedure extracts samples (soil, litter, etc.) using a pH solution at 5.0+/−0.5 and a 20× dilution of the solution for 18 hours +/−2 hours. The leachate is then analyzed for the target compound, in this case, soluble phosphorus.

Results: Phosphorus levels in the untreated Control House 2 were:

(A) 97.9 mg/l;

(B) 87.1 mg/l; and (C) 94.9 mg/l.

(There was a 3.1% reduction in soluble phosphorus, which is believed to likely be attributable to standard sampling variation.) Test House 1 had phosphorus levels of:
(A) 111.0 mg/l;
(B) 94.6 mg/l; and
(C) 54.6 mg/l.
Test House 1 showed a 50.8% reduction in soluble phosphorus.

Experimental evidence shows that analytical leachate methods, especially EPA SW846-Method 1312 (Synthetic Precipitation Leaching Procedure), do not cause release of bound phosphorus and nitrates from treated chicken litter containing phosphorus and nitrate. The chemical reaction between such components and the treatment composition results in the formation of a product that chemically binds phosphate and nitrate essentially permanently. The soluble phosphorus and nitrates are chemically bonded in a two-step reaction sequence. Each component of the silicate solution must be added in the order stated, and is not deviated from that sequence. Neither reaction alone will result in the permanent binding of the metal components. The reaction sequence is believed to involve the addition of a metal sulfate in the presence of soluble phosphorus, followed by the addition of an aqueous alkali metal silicate to form a substituted metal phospho-silicate. A polymerized silicate occurs with the loss of water upon drying. The reaction is irreversible, and cannot be re-hydrated.

We claim:

1. A method of using an activator for a composition comprising sodium silicate at a concentration in the range of between about 1% and 42% by weight of said treatment composition, propylene glycol at a concentration of about 1% by weight of the treatment composition, and a phosphate ester at a concentration in the range of between about 1% and 5% by weight of the treatment composition in amounts effective to chemically bind the soluble phosphorus of animal waste into a stable complex thereby reducing the availability of the soluble phosphorus by up to 86%, said activator comprising magnesium sulfate, said method of use comprising the initial step of dispersing the activator upon the animal waste.

2. A method described in claim 1, further comprising the step of mixing said animal waste and said dispersed activator.

3. A method described in claim 2, further comprising the step of dispersing, upon the activator-animal waste mixture, said treatment composition.

4. A method described in claim 3, further comprising the step of mixing the activator-animal waste and the treatment composition mixture.

5. A method described in claim 4, further comprising the step of allowing the activator-animal waste-composition mixture to dry.

6. A method described in claim 1, wherein said magnesium sulfate is in aqueous solution at a concentration of about 5% by weight of said activator solution.

7. A method described in claim 1, wherein said magnesium sulfate is in aqueous solution at a concentration of about 10% by weight of said activator solution.

8. A method described in claim 1, wherein said magnesium sulfate is in aqueous solution at a concentration of between about 1% and 20% by weight of said activator solution, said animal waste comprising chicken litter.

9. A method described in claim 1, said activator comprising magnesium sulfate in aqueous solution at a concentration in the range of about 5% and 10% by weight of said activator solution, said composition comprising aqueous solution of sodium silicate at a concentration in the range of between about 19% and 23% by weight, propylene glycol at a concentration in the range of between about 1% and 5% by weight and ester of organo-phosphoric acid at a concentration in the range of between about 1% and 5% by weight.

10. An activator described in claim 1, said activator comprising magnesium sulfate in aqueous solution at a concentration of about 10% by weight of said activator solution, said composition comprising aqueous sodium silicate at a concentration of about 20.8% by weight, propylene glycol at a concentration of about 1% by weight and ester of organo-phosphoric acid at a concentration of about 1%.

* * * * *